(12) United States Patent
Griffiths et al.

(10) Patent No.: US 7,098,240 B2
(45) Date of Patent: Aug. 29, 2006

(54) COMPOUNDS

(75) Inventors: David Griffiths, Macclesfield (GB); Craig Johnstone, Macclesfield (GB)

(73) Assignee: AstraZeneca AB, (SE)

( * ) Notice: Subject to any disclaimer, the term of this patent is extended or adjusted under 35 U.S.C. 154(b) by 369 days.

(21) Appl. No.: 10/484,645

(22) PCT Filed: Jul. 19, 2002

(86) PCT No.: PCT/SE02/01402

§ 371 (c)(1),
(2), (4) Date: Jan. 22, 2004

(87) PCT Pub. No.: WO03/010163

PCT Pub. Date: Feb. 6, 2003

(65) Prior Publication Data

US 2004/0235821 A1    Nov. 25, 2004

(30) Foreign Application Priority Data

Jul. 25, 2001   (SE) ..................... 0102617

(51) Int. Cl.
*A61K 31/38*    (2006.01)
*C07D 409/00*   (2006.01)
*C07D 333/36*   (2006.01)

(52) U.S. Cl. ............... 514/447; 514/444; 549/60; 549/63; 549/59

(58) Field of Classification Search ............. 514/444, 514/447; 549/59, 60, 63
See application file for complete search history.

(56) References Cited

U.S. PATENT DOCUMENTS

| | | | |
|---|---|---|---|
| 6,048,880 A * | 4/2000 | Kawai et al. ............ | 514/336 |
| 6,380,214 B1 * | 4/2002 | Gant et al. ............. | 514/314 |
| 6,699,854 B1 * | 3/2004 | Wang et al. ............ | 514/183 |
| 6,809,088 B1 * | 10/2004 | Chabrier de Lassauniere et al. ...... | 514/183 |

FOREIGN PATENT DOCUMENTS

| | | |
|---|---|---|
| EP | 0 202 538 A1 | 11/1986 |
| EP | 0 853 083 A1 | 7/1998 |
| EP | 0 908 456 A1 | 4/1999 |
| GB | 1468012 | 3/1977 |
| WO | WO 98/02430 | 1/1998 |
| WO | WO 98/54116 | 12/1998 |
| WO | WO 99/46244 | 9/1999 |
| WO | WO 00/71532 | 11/2000 |
| WO | WO 01/98290 | 12/2001 |
| WO | WO 02/30353 | 4/2002 |

OTHER PUBLICATIONS

U.S. Appl. No. 09/868,884, filed Feb. 5, 2002, Baxter et al.
U.S. Appl. No. 10/484,569, filed Jan. 22, 2004, Faull et al.
Zayed et al., "Studies on 5-Aminopyrazole Derivatives. Synthesis of Some New Fused Pyrazole Derivatives", *Monatshefte für Chemie* 115:431-436 (1984).

* cited by examiner

*Primary Examiner*—Deborah C. Lambkin
(74) *Attorney, Agent, or Firm*—Fish & Richardson P.C.

(57) ABSTRACT

The invention relates to thiophene carboxamides of formula (I), wherein $R_1$, $R_2$, $R_3$, A, n and X are as defined in the specification, processes and intermediates used in their preparation, pharmaceutical compositions containing them and their use in therapy

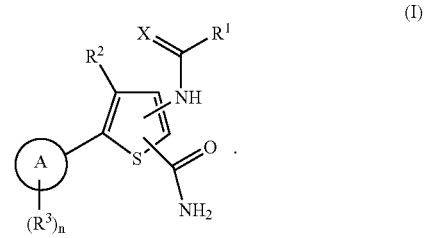

(I)

15 Claims, No Drawings

COMPOUNDS

This application claims priority under 35 U.S.C. §371 to a national phase filing of international application number PCT/SE02/01402, filed Jul. 19, 2002, which claims priority to SE 0102617-8, filed Jul. 25, 2001. These applications are incorporated by reference herein.

FIELD OF THE INVENTION

The present invention relates to thiophene carboxamide derivatives, processes and intermediates used in their preparation, pharmaceutical compositions containing them and their use in therapy.

BACKGROUND OF THE INVENTION

The NF-κB (nuclear factor κB) family is composed of homo- and heterodimers of the Rel family of transcription factors. A key role of these transcription factors is to induce and coordinate the expression of a broad spectrum of pro-inflammatory genes including cytokines, chemokines, interferons, MHC proteins, growth factors and cell adhesion molecules (for reviews see Verma et. al., Genes Dev. 9:2723–35, 1995; Siebenlist et. al., Ann. Rev. Cell. Biol. 10:405–455, 1994; Bauerle and Henkel, Ann. Rev. Immunol., 12:141–179, 1994; Barnes and Karin, New Engl. J. Med., 336:1066–1071, 1997).

The most commonly found Rel family dimer complex is composed of p50 NFkB and p65 RelA (Baeuerle and Baltimore, Cell 53:211–217, 1988; Baeuerle and Baltimore, Genes (Dev. 3:1689–1698, 1989). Under resting conditions NF-κB dimers are retained in the cytoplasm by a member of the IκB family of inhibitory proteins (Beg et. al., Genes Dev., 7:2064–2070, 1993; Gilmore and Morin, Trends Genet. 9:427–433, 1993; Haskil et. al., Cell 65:1281–1289, 1991). However, upon cell activation by a variety of cytokines or other external stimuli, IκB proteins become phosphorylated on two critical serine residues (Traenckner et. al., EMBO J., 14:2876, 1995) and are then targeted for ubiquitination and proteosome-mediated degradation (Chen, Z. J. et. al., Genes and Dev: 9:1586–1597, 1995; Scherer, D. C. et. al., Proc. Natl. Acad. Sci. USA 92:11259–11263, 1996; Alkalay, I. et. al., Proc. Natl. Acad. Sci. USA 92:10599–10603, 1995). The released NF-κB is then able to translocate to the nucleus and activate gene transcription (Beg et. al., Genes Dev., 6:1899–1913, 1992).

A wide range of external stimuli have been shown to be capable of activating NF-κB (Baeuerle, P. A., and Baichwal, V. R., Adv. Immunol., 65:111–136, 1997). Although the majority of NF-κB activators result in IκB phosphorylation, it is clear that multiple pathways lead to this key event. Receptor-mediated NF-κB activation relies upon specific interactions between the receptor and adapter/signalling molecules (for example, TRADD, RIP, TRAF, MyD88) and associated kinases (IRAK, NIK) (Song et. al., Proc. Natl. Acad. Sci. USA 94:9792–9796, 1997; Natoli et. al., JBC 272:26079–26082, 1997). Environmental stresses such as UV light and γ-radiation appear to stimulate NF-κB via alternative, less defined, mechanisms.

Recent publications have partially elucidated the NF-κB activation. This work has identified three key enzymes which regulate specific IκB/NF-κB interactions: NF-κB inducing kinase (NIK) (Boldin et. al., Cell 85:803–815, 1996), IκB kinase-1 (IKK-1) (Didonato et. al., Nature 388: 548,1997; Regnier at al., Cell 90:373 1997) and IκB kinase-2 (IKK-2) (Woronicz et. al., Science 278:866, 1997; Zandi et. al., Cell 91:243, 1997).

NIK appears to represent a common mediator of NF-κB signalling cascades triggered by tumour necrosis factor and interleukin-1, and is a potent inducer of IκB phosphorylation. However NIK is unable to phosphorylate IκB directly.

IKK-1 and IKK-2 are thought to lie immediately downstream of NIK and are capable of directly phosphorylating all three IκB sub-types. IKK-1 and IKK-2 are 52% identical at the amino acid level but appear to have similar substrate specificities; however, enzyme activities appear to be different: IKK-2 is several-fold more potent than IKK-1. Expression data, coupled with mutagenesis studies, suggest that IKK-1 and IKK-2 are capable of forming homo- and heterodimers through their C-terminal leucine zipper motifs, with the heterodimeric form being preferred (Mercurio et. al., Mol. Cell Biol., 19:1526, 1999; Zandi et. al., Science; 281:1360, 1998; Lee et. al, Proc. Natl. Acad. Sci. USA 95:9319, 1998).

NIK, IKK-1 and IKK-2 are all serine/threonine kinases. Recent data has shown that tyrosine kinases also play a role in regulating the activation of NF-κB. A number of groups have shown that TNF-α induced NF-κB activation can be regulated by protein tyrosine phosphatases (PTPs) and tyrosine kinases (Amer et. al., JBC 273:29417–29423, 1998; Hu et. al., JBC 273:33561–33565, 1998; Kaekawa et. al., Biochem. J. 337:179–184, 1999; Singh et. al., JBC 271 31049–31054, 1996). The mechanism of action of these enzymes appears to be in regulating the phosphorylation status of IκB. For example, PTP1B and an unidentified tyrosine kinase appear to directly control the phosphorylation of a lysine residue (K42) on IκB-α, which in turn has a critical influence on the accessibility of the adjacent serine residues as targets for phosphorylation by IKK.

Several groups have shown that IKK-1 and IKK-2 form part of a 'signalosome' structure in association with additional proteins including IKAP (Cohen et. al., Nature 395: 292–296, 1998; Rothwarf et. al., Nature 395:297–300, 1998), MEKK-1, putative MAP kinase phosphatase (Lee et. al., Proc. Natl. Acad. Sci. USA 95:9319–9324, 1998), as well as NIK and IκB. Data is now emerging to suggest that although both IKK-1 and IKK-2 associate with NIK, they are differentially activated, and therefore might represent an important integration point for the spectrum of signals that activate NF-κB. Importantly, MEKK-1 (one of the components of the putative signalosome and a target for UV light, LPS induced signalling molecules and small GTPases) has been found to activate IKK-2 but not IKK-1. Similarly, NIK phosphorylation of IKK-1 results in a dramatic increase in IKK-1 activity but only a small effect on IKK-2 (for review, see Mercurio, F., and Manning, A. M., Current Opinion in Cell Biology, 11:226–232, 1999).

Inhibition of NF-κB activation is likely to be of broad utility in the treatment of inflammatory disease.

There is accumulating evidence that NF-κB signalling plays a significant role in the development of cancer and metastasis. Abnormal expression of c-Rel1, NF-κB2 or IκBα have been described in a number of tumour types and tumour cell lines, and there is now data to show that constitutive NF-κB signalling via IKK2 takes place in a wide range of tumour cell lines. This activity has been linked to various upstream defects in growth factor signalling such as the establishment of autocrine loops, or the presence of oncogene products e.g. Ras, AKT, Her2, which are involved in the activation of the IKK complex. Constitutive NF-κB activity is believed to contribute to oncogenesis through activation of a range of anti-apoptotic genes e.g. A1/Bfi-1, IEX-1, XIAP, leading to the suppression of cell death pathways, and transcriptional upregulation of cyclin D1 which promotes cell growth. Other data indicate that this pathway is also likely to be involved in the regulation of cell adhesion and cell surface proteases. This suggests a possible additional role for NF-κB activity in the development of metastasis. Evidence confirming the involvement of NF-κB activity in oncogenesis includes the inhibition of tumour cell growth in vitro and in vivo on expression of a modified form of IκBα (super-repressor IκBα).

In addition to the constitutive NF-κB signalling observed in many tumour types, it has been reported that NF-κB is also activated in response to certain types of chemotherapy. Inhibition of NF-κB activation through expression of the super-repressor form of IκBα in parallel with chemotherapy treatment has been shown to enhance the antitumour effect of the chemotherapy in xenograft models. NF-κB activity is therefore also implicated in inducible chemoresistance.

DISCLOSURE OF THE INVENTION

According to the present invention, there is provided a compound of formula (I)

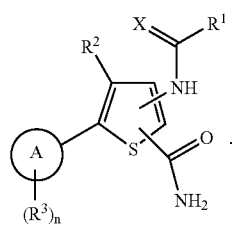

in which:

$R^1$ represents $NH_2$ or $R^1$ represents a methyl group optionally substituted by one or more groups selected independently from $C_1$–$C_4$ alkyl, $C_3$–$C_6$ cycloalkyl, halogen, hydroxyl, $C_1$–$C_4$ alkoxy, $S(O)_v CH_3$ and $NR^4R^5$.

X represents O or S;

$R^2$ represents hydrogen, halogen, cyano, nitro, $-NR^6R^7$, $-CONR^6R^7-COOR$, $-NR^6$ $COR^7$, $-S(O)_m R^6$, $-SO_2NR^6R^7-NR^6SO_2$ $R^7$, $C_1$–$C_2$ alkyl, trifluoromethyl, $C_2$–$C_3$ alkenyl, $C_2$–$C_3$ alkynyl, trifluoromethoxy, $C_1$–$C_2$ alkoxy or $C_1$–$C_2$ alkanoyl;

A represents a fused bicyclic ring system wherein one ring is a phenyl ring or a 5- to 7-membered heteroaromatic ring containing one to three heteroatoms selected independently is from O N and S; and the other ring is either a fused phenyl ring or a fused 5- to 7-membered heteroaromatic ring containing one to three heteroatoms selected independently from O, N and S, or a fused 5- to 7-membered saturated ring optionally incorporating one to three heteroatoms selected independently from oxygen, nitrogen and sulphur; said fused bicyclic ring system being optionally substituted by one or more substituents selected independently from halogen, cyano, nitro, $-NR^8$ $COR^9$, $-S(O)_r R^8$, $-SO_2NR^8R^9$, $-NR^8$ $SO_2R^9$ and $C_1$–$C_6$ alkyl;

n represents an integer 0, 1 or 2; and when n represents 2, each $R^3$ group may be selected independently;

$R^3$ represents a group $-W-Y-Z$ wherein:

W represents O, $S(O)_r$, $NR^{13}$, $CH_2$, $-CH_2-O-$ or a bond;

Y represents a bond or Y represents a group $-(CH_2)_p-X-(CH_2)_q-$ wherein p and q independently represent an integer 0, 1 or 2; and X represents O, $-CO-$ or $CR^{14}R^{15}$;

$R^{14}$ and $R^{15}$ independently represent H, $CH_3$ or F;

or $R^{14}$ represents H or $CH_3$ and $R^{15}$ represents hydroxyl or $OCH_3$;

or the group $CR^{14}R^{15}$ together represents a $C_3$–$C_6$ cycloalkyl ring;

Z represents:

(a) a phenyl ring or a 5- or 6-membered heteroaromatic ring containing one to three heteroatoms selected independently from O, N and S; said phenyl or heteroaromnatic ring being optionally substituted by one or more substituents selected independently from halogen, cyano, $-NR^{16}R^{17}$, $-CONR^{16}R^{17}$, $-COOR^{16}$, $-COR^{16}-NR^{16}$ $COR^{17}$, $-S(O)_u R^{16}$, $-SO_2NR^{16}R^{17}$, $-NR^{16}SO_2R^{17}$, hydroxyl, $C_2$–$C_6$ alkenyl, $C_2$–$C_6$ alkynyl, $C_1$–$C_6$ alkyl and $C_1$–$C_6$ alkoxy; said alkyl or alkoxy group being optionally further substituted by one or more groups selected from halogen, cyano, hydroxyl, $C_1$–$C_4$ alkoxy and $NR^{18}$ $R^{19}$; or (b) a saturated 3- to 7-membered ring optionally incorporating one or two heteroatoms selected independently from O, N and S, and optionally incorporating a carbonyl group; said saturated ring being optionally substituted by one or more substituents selected independently from halogen, cyano, $-NR^{16}R^{17}$, $-CONR^{16}R^{17}$, $-COOR^{16}$, $-COR^{16}$ $-NR^{16}$ $COR^{17}$, $-S(O)_u R^{16}$, $-SO_2NR^{16}R^{17}$, $-NR^{16}$ $SO_2R^{17}$, hydroxyl, $C_2$–$C_6$ alkenyl, $C_2$–$C_6$ alkynyl, $C_1$–$C_6$ alkyl and $C_1$–$C_6$ alkoxy; said alkyl or alkoxy group being optionally further substituted by one or more groups selected from halogen, cyano, hydroxyl, $C_1$–$C_4$ alkoxy and $NR^{18}R^{19}$; or (c) Z represents hydroxyl, $C_1$–$C_6$ alkoxy, $CF_3$, $CHF_2$, $CH_2F$ or $NR^{20}R^{21}$ where $R^{20}$ and $R^{21}$ are independently hydrogen or $C_1$–$C_6$ alkyl optionally substituted by $C_1$–$C_4$ alcoxy;

$R^4$ and $R^5$ independently represent H or $C_1$–$C_4$ alkyl, or the group $NR^4R^5$ represents a 5- or 6-membered saturated azacyclic ring optionally containing a further O, S or $NR^{23}$ group; where $R^{23}$ is hydrogen or $C_1$–$C_4$ alkyl;

$R^6$ and $R^7$ independently represent H or $C_1$–$C_2$ allyl;

$R^8$ and $R^9$ independently represent H or $C_1$–$C_6$ alkyl;

$R^{13}$ represents H or $C_1$–$C_4$ alkyl;

$R^{16}$ and $R^{17}$ independently represent H or $C_1$–$C_6$ alkyl; or the group $NR^{16}R^{17}$ represents a 5- or 6-membered saturated azacyclic ring optionally containing a further O, S or $NR^{24}$ group; where $R^{24}$ is hydrogen or $C_1$–$C_6$ alkyl;

$R^{18}$ and $R^{19}$ independently represent H or $C_1$–$C_4$ alkyl; or the group $NR^{18}R^{19}$ represents a 5- or 6-membered saturated azacyclic ring optionally containing a further O, S or $NR^{25}$ group; where $R^{25}$ is hydrogen or $C_1$–$C_4$ alkyl;

m, r, s, u and v independently represent an integer 0, 1 or 2;

and pharmaceutically acceptable salts thereof.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

In one embodiment, X represents oxygen.

In another embodiment, $R^1$ represents $CH_3$ or $NH_2$. In a more particular embodiment, $R^1$ represents $NH_2$.

The compounds of formula (I) and their pharmaceutically acceptable salts have the advantage that they are inhibitors of the enzyme IKK2.

The invention further provides a process for the preparation of compounds of formula (I) or a pharmaceutically acceptable salt, enantiomer or racemate thereof.

According to the invention there is also provided a compound of formula (I), or a pharmaceutically acceptable salt thereof, for use as a medicament.

Another aspect of the invention provides the use of a compound of formula (I) or a pharmaceutically acceptable salt thereof, in the manufacture of a medicament, for the treatment or prophylaxis of diseases or conditions in which inhibition of IKK2 activity is beneficial.

Another aspect of the invention provides the use of a compound of formula (I) or a pharmaceutically acceptable salt thereof, in the manufacture of a medicament, for the treatment or prophylaxis of inflammatory disease.

According to the invention, there is also provided a method of treating, or reducing the risk of, diseases or conditions in which inhibition of IKK2 activity is beneficial which comprises administering to a person suffering from or at risk of, said disease or condition, a therapeutically effective amount of a compound of formula (I), or a pharmaceutically acceptable salt thereof.

There is also provided a method of treating, or reducing the risk of; inflammatory; disease in a person suffering from or at risk of, said disease, wherein the method comprises administering to the person a therapeutically effective amount of a compound of formula (I) or a pharmaceutically acceptable salt thereof.

In particular embodiments, the fused bicyclic ring system A represents optionally substituted quinoline, indole, benzothiophene, benzofuran, tetrahydroisoquinoline, 1,3-benzodioxolane (methylenedioxyphenyl) and 1,4-benzodioxane (ethylenedioxyphenyl).

In one embodiment, the group $R^2$ in formula (I) represents H, halogen or $C_1$–$C_2$ alkyl. In another embodiment, the group $R^2$ represents H or methyl. In yet another embodiment, the group $R^2$ in formula(I) represents H.

Particular compounds of the invention include those exemplified herein:

2-[(aminocarbonyl)amino]-5-(2-benzofuranyl)-3-thiophenecarboxamide;
2-[(aminocarbonyl)amino]-5-(3-quinolinyl)-3-thiophenecarboxamide;
2-[(aminocarbonyl)amino]-5-(8-quinolinyl)-3-thiophenecarboxamide;
2-[(aminocarbonyl)amino]-5-(2-benzothiophenyl)-3-thiophenecarboxamide;
2-[(aminocarbonyl)amino]-5-(3-benzothiophenyl)-3-thiophenecarboxamide;
2-[(aminocarbonyl)amino]-5-(5-indolyl)-3-thiophenecarboxamide;
2-[(aminocarbonyl)amino]-4-methyl-5-(1,4-benzodioxan-6-yl)-3-thiophenecarboxamide;
2-[(aminocarbonyl)amino]-4-methyl-5-(3-indolyl)-3-thiophenecarboxamide;
2-[(aminocarbonyl)amino]-4-methyl-5-(1,3-benzodioxo-5-yl)-3-thiophenecarboxamide;
2-[(aminocarbonyl)amino]-5-(1H-indol-2-yl)thiophene-3-carboxamide;
3-[(aminocarbonyl)amino]-5-(1-benzothien-3-yl)thiophene-2-carboxamide;
2-[(aminocarbonyl)amino]-5-(2-morpholin-4-ylmethyl-benzo[b]thiophen-5-yl)thiophene-3-carboxamide;
2-[(aminocarbonyl)amino]-5-[4-(2-morpholin-4-ylethoxy)-1-benzothien-2-yl]-3-thiophenecarboxamide;
2-[(aminocarbonyl)amino]-5-{2-[4-methylphenylsulphonyl]-1,2,3,4-tetrahydro isoquinolin-6-yl}thiophene-3-carboxamide;
3-[(aminocarbonyl)amino]-5-(1-benzothien-2-yl)thiophene-2-carboxamide;

and pharmaceutically acceptable salts thereof.

Unless otherwise indicated, the term "$C_1$–$C_6$ alkyl" referred to herein denotes a straight or branched chain alkyl group having from 1 to 6 carbon atoms. Examples of such groups include methyl, ethyl, n-propyl, i-propyl, n-butyl, i-butyl and t-butyl. The terms "$C_1$–$C_2$ alkyl" and "$C_1$–$C_4$ alkyl" are to be interpreted analogously.

Unless otherwise indicated, the term "$C_2$–$C_3$ alkenyl" referred to herein denotes a straight or branched chain alkyl group having 2 or 3 carbon atoms incorporating at least one carbon-carbon double bond. Examples of such groups include ethenyl and propenyl. The term "$C_2$–$C_6$ alkenyl" is to be interpreted analogously.

Unless otherwise indicated, the term "$C_2$–$C_3$ alkynyl" referred to herein denotes a straight chain alkyl group having 2 or 3 carbon atoms incorporating one carbon-carbon triple bond. Examples of such groups include ethynyl and propynyl. The term "$C_2$–$C_6$ alkynyl" is to be interpreted analogously.

Unless otherwise indicated, the term "$C_3$–$C_6$ cycloalkyl" referred to herein denotes a saturated carbocyclic ring having from 3 to 6 carbon atoms. Examples of such groups include cyclopropyl, cyclopentyl and cyclohexyl.

Unless otherwise indicated, the term "$C_1$–$C_4$ alkoxy" referred to herein denotes a straight or branched chain alkoxy group having 1 to 4 carbon atoms. Examples of such groups include methoxy, ethoxy and isopropoxy. The terms "$C_1$–$C_2$ alkoxy" and "$C_1$–$C_6$ alkoxy" are to be interpreted analogously.

Unless otherwise indicated, the term "$CC_1$–$C_2$ alkanoyl" referred to herein denotes a formyl or acetyl group.

Unless otherwise indicated, the term "halogen" referred to herein denotes fluoro, chloro, bromo and iodo.

Examples of a 5- to 7-membered heteroaromatic ring containing one to three heteroatoms selected independently from O, N and S include furan, thiophene, pyrrole, oxazole, isoxazole, thiazole, isothiazole, imidazole, pyrazole, triazole, pyridine, pyridazine, pyrimidine and pyrazine. The term "a 5- or 6-membered heteroaromatic ring containing one to three heteroatoms selected independently from O, N and S" is to be interpreted is, analogously.

Examples of a saturated 5- to 7-membered ring optionally incorporating one to three heteroatoms selected independently from O, N and S include cyclopentyl, cyclohexyl, tetrahydrofuran, pyrrolidine, piperidine, piperazine and morpholine.

Examples of a fused bicyclic ring system wherein one ring is a phenyl ring or a 5- to 7-membered heteroaromatic ring containing one to three heteroatoms selected independently from O, N and S; and the other ring is either a fused phenyl ring or a fused 5- to 7-membered heteroaromatic ring containing one to three heteroatoms selected independently from O, N and S; or a fused 5- to 7-membered saturated ring optionally incorporating one to three heteroatoms selected independently from oxygen, nitrogen and sulphur include naphthyl, quinoline, isoquinoline, tetrahydroisoquinoline, indole, benzothiophene, benzofuran, benzimidazole, 1,3-benzodioxolane (methylenedioxyphenyl) and 1,4-benzodioxane (ethylenedioxyphenyl).

Examples of a 5- or 6-membered saturated azacyclic ring optionally containing a fer O, or NR group include pyrrolidine, piperidine, piperazine and morpholine.

Examples of a saturated 3- to 7-membered ring optionally incorporating one or two heteroatoms selected independently from O, N and S, and optionally incorporating a carbonyl group include cyclopropyl, cyclohexyl, pyrrolidine, piperidine, morpholine, tetrahydrofuran, piperidin-2-one and piperidine-4-one.

According to the invention there is also provided a process for the preparation of a compound of formula (I) or a pharmaceutically acceptable salt, enantiomer or racemate thereof which comprises:

(a) reaction of a compound of formula (II):

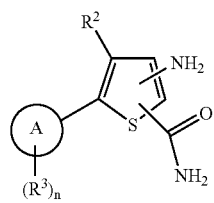

(II)

wherein A, $R^2$, $R^3$ and n are as defined in formula (I) with an isocyanate or an isothiocyanate or an acyl derivative, $R^1$—CO-L where L is a leaving group; or (b) reaction of compound of formula (III)

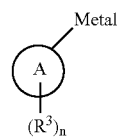

(III)

wherein $R^3$ n and A are as defined in formula (I) with a compound of formula (IV)

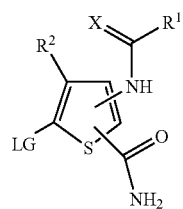

(IV)

wherein X, $R^1$ and $R^2$ are as defined in formula (I) and LG represents a leaving group; or (c) reaction of compound of formula (V)

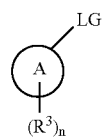

(V)

wherein $R^3$, n and A are as defined in formula (I) and LG represents a leaving group, with a compound of formula (VI)

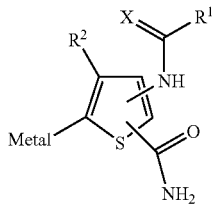

(VI)

wherein X, $R^1$ and $R^2$ are as defined in formula (I);

and where necessary converting the resultant compound of formula(I), or another salt thereof, into a pharmaceutically acceptable salt thereof, or converting the resultant compound of formula (I) into a further compound of formula (I); and where desired converting the resultant compound of formula (I) into an optical isomer thereof.

In process (a), suitable isocyanate reagents include trimethylsilylisocyanate, trimethylsilylisothiocyanate, chlorosulphonylisocyanate, trichloroacetylisocyanate and sodium isocyanate. The reaction with trimethylsilylisocyanate or trimethylsilylisothiocyanate can be carried out in a solvent such as dichloromethane/dimethylformamide at a suitable elevated temperature, for example, at the reflux temperature of the reaction mixture. The reaction with chlorosulphonylisocyanate can be carried out in a solvent such as toluene at ambient temperature. The reaction with sodium isocyanate can be carried out in a suitable solvent system such as aqueous acetic acid at ambient temperature. The trichloroacetylisocyanate reaction can be carried out in a suitable solvent system such as acetonitrile at ambient temperature, and subsequently treating the mixture with ammonia to give compounds of the general formula (I). Suitable acyl derivatives of formula $R^1$—CO—L include acyl halides, particularly acyl chlorides, and acid anhydrides. Reactions with such acyl derivatives are generally carried out at ambient temperature in a suitable solvent such as pyridine, or in a solvent such as dichloromethane in the presence of a suitable base such as triethylamine or pyridine. Compounds of formula (I) wherein X represents O may subsequently be converted into corresponding compounds of formula (I) wherein X represents S by reaction with, for example, Lawesson's reagent.

In processes (b) and (c), the compounds of formulae (III) and (IV) or of formulae (V) and (VI) are reacted together under catalysis provided by a complex of a transition metal such as palladium or nickel. In compounds of formulae (III) and (VI), under appropriate conditions, "metal" can be a metal or semi-metal such as magnesium, zinc, copper, tin, silicon, zirconium, aluminium or boron. Suitable leaving groups include iodo, bromo, chloro, triflate or phosphonate.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the addition and removal of one or more protecting groups.

The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or racemate thereof with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed vacuo or by freeze drying. The reaction may also be a metathetical process or it may be carried out on an ion exchange resin.

Compounds of formula (II) can be prepared by standard chemistry described in the literature [for example, J. Het. Chem. 36, 333 (1999)] or by reaction of compounds of formula (VII):

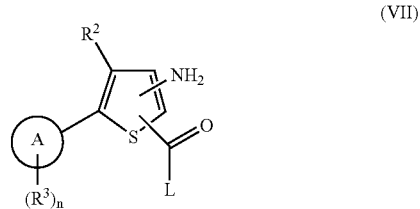

(VII)

where A, R², R³ and n are as defined in formula (I), and L represents a leaving group, with ammonia. Suitable groups L include halogen, in particular chloro.

Compounds of formula (VII) where L is halo can be prepared from the corresponding compound of formula (VIII):

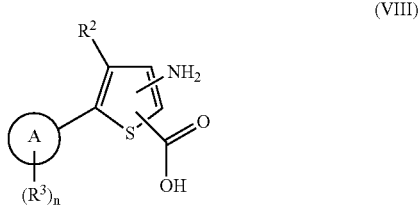

(VIII)

where A, R², R³ and n are as defined in formula (I), by treating with a halogenating agent such as thionyl chloride.

Compounds of formulae (II), (I), (V), (VI) and (VI) are commercially available or can be prepared using standard chemistry as exemplified herein.

Certain novel intermediate compounds form a further aspect of the invention.

The compounds of formula (I) have activity as pharmaceuticals, in particular as IKK2 enzyme inhibitors, and may be used in the treatment (therapeutic or prophylactic) of conditions/diseases in human and non-human animals in which inhibition of IKK2 is beneficial. Examples of such conditions/diseases include inflammatory diseases or diseases with an inflammatory component. Particular diseases include inflammatory arthritides including rheumatoid arthritis, osteoarthritis, spondylitis, Reiters syndrome, psoriatic arthritis, lupus and bone resorptive disease; multiple sclerosis, inflammatory bowel disease including Crohn's disease; asthma, chronic obstructive pulmonary disease, emphysema, rhinitis, myasthenia gravis, Graves' disease, allograft rejection, psoriasis, dermatitis, allergic disorders, immune complex diseases, cachexia, ARDS, toxic shock, heart failure, myocardial infarcts, atherosclerosis, reperfusion injury, AIDS, cancer and disorders characterised by insulin resistance such as diabetes, hyperglycemia, hyperinsulinemia, dyslipidemia, obesity, polycystic ovarian disease, hypertension, cardiovascular disease and Syndrome X.

The reported roles of NF-κB in both oncogenesis and chemoresistance suggest that inhibition of this pathway through the use of an IKK2 inhibitor, such as a small molecule IKK2 inhibitor, could provide a novel monotherapy for cancer and/or an important adjuvant therapy for the treatment of chemoresistant tumours.

We are particularly interested in diseases selected from asthma, rheumatoid arthritis, psoriasis, inflammatory bowel disease including Crohn's disease, multiple sclerosis, chronic obstructive pulmonary disease, bone resorptive disease, osteoarthritis, diabetes/glycaemic control and cancer.

Thus, the present invention provides a compound of formula (I), or a pharmaceutically acceptable salt thereof, as hereinbefore defined for use in therapy.

In a further aspect, the present invention provides the use of a compound of formula (I), or a pharmaceutically acceptable salt thereof; as hereinbefore defined in the manufacture of a medicament for use in therapy.

In a still further aspect, the present invention provides the use of a compound of formula (I), or a pharmaceutically acceptable salt thereof; as hereinbefore defined in the manufacture of a medicament for the treatment of diseases or conditions in which modulation of the IKK2 enzyme activity is beneficial.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating an IKK2 mediated disease which comprises administering to a patient a therapeutically effective amount of a compound of formula (I), or a pharmaceutically acceptable salt thereof, as hereinbefore defined.

The invention also provides a method of treating an inflammatory disease, especially asthma, rheumatoid arthritis or multiple sclerosis, in a patient suffering from, or at risk of, said disease, which comprises administering to the patient a therapeutically effective amount of a compound of formula (I), or a pharmaceutically acceptable salt thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Conventional procedures for the selection and preparation of suitable pharmaceutical formulations are described in, for example, "Pharmaceuticals—The Science of Dosage Form Designs", M. E. Aulton, Churchill Livingstone, 1988.

The invention is illustrated, but in no way limited, by the following examples:

EXAMPLE 1

2-[(Aminocarbonyl)amino]-5-(2-benzofuranyl)-3-thiophenecarboxamide a) 2-Amino-3-thiophenecarboxamide The title compound was synthesised as follows using the method described in Bull.Soc.Chim.France 2804 (1974).

A suspension of 2,5-dihydroxy-1,4-dithiane (25 g) and cyanoacetamide (19.3 g) in ethanol (120 ml) was stirred and heated to 50° C. Triethylamine (9.2 ml) was added over 15 minutes and the mixture was stirred at 50° C. for a further 2 h. After cooling in ice, the solid was filtered off and dried (21.4 g).

MS (ES) 143(4+H)$^+$.

b) 2-[(Aminocarbonyl)amino]-3-thiophenecarboxamide

2-Amino-3-thiophencarboxamide (0.44 g) was suspended in acetonitrile (25 ml) and trichloroacetylisocyanate (0.2 ml) added dropwise with stirring over 10 minutes. Stirring was continued for a further 3 h at room temperature and then a solution of ammonia in methanol (10 ml of a 2M solution) was added and stirring was continued for a further 2 h. The solvent was evaporated and the residue treated with water. The resultant solid was filtered off and washed with more water. Trituration with ether gave the title urea (0.2 g).

MS (ES) 186 (M+H)$^+$.

c) 2-[(Aminocarbonyl)amino]-5-bromo-3-thiophenecarboxamide

2-[(Aminocarbonyl)amino]-3-thiophenecarboxamide (1.0 g) was dissolved in acetic acid (20 ml) and a solution of bromine (0.35 ml) in acetic acid (5 ml) was added over 5 minutes with rapid stirring. The mixture was stirred for 90 minutes and then added to water (50 ml). The product was filtered off and washed with water and dried under vacuum (0.55 g).

MS (ES) 262/264 (M–H)$^-$.

$^1$HNMR (DMSO-D6) 7.15 (m, 1H), 7.35 (m, 1H), 7.8 (s, 1H), 7.9 (m, 1H), 10.63 (brs, 1H).

d) 2-[(Aminocarbonyl)amino]-5-(2-benzofuranyl)-3-thiophenecarboxamide

A solution of 2-[(aminocarbonyl)amino]-5-bromo-3-thiophenecarboxamide (0.26 g), sodium carbonate (0.23 g) and benzofuran-2-boronic acid (0.32 g) in dimethoxyethane (60 ml) and water (2 ml) was, purged with argon for 10 minutes.

Tetrakis(triphenylphosphine)palladium (0.2 g) was then added and the mixture refluxed with stirring for 7 h. After cooling, the mixture was screened and evaporated. The residue was partitioned between ethyl acetate and 3N sodium carbonate solution and the solid interface layer was filtered off (0.2 g).

MS (ES) 300 (M–H).

$^1$H NMR (DMSO-D6) 6.9 (s, 1H), 7.05 (m, 2H), 7.2 (m, 2H), 7.3 (m, 1H), 7.6 (m, 3H), 7.8 (m, 2H), 11.15 (brs, 1H).

EXAMPLE 2

2-[(Aminocarbonyl)amino]-5-(3-quinolinyl)-3-thiophenecarboxamide

Prepared by the method of Example 1 (d) but using quinoline-3-boronic acid.

MS (ES) 311 (M–H)$^-$.

$^1$H NMR (DMSO-D6) 7.0, (m, 2H), 7.4 (m, 1H), 7.6 (m, 2H), 7.65 (m, 2H), 8.0 (m, 2H), 8.4 (s, 1H), 9.15 (s, 1H), 11.06 (brs, 1H).

EXAMPLE 3

2-[(Aminocarbonyl)amino]-5-(8-quinolinyl)-3-thiophenecarboxamide

Prepared by the method of Example 1 (d) but using quinoline-8-boronic acid

MS (ES) 311 (M–H)$^-$.

$^1$H NMR (DMSO-D6) 6.9 (m, 2H), 7.2 (m, 1H), 7.6 (m, 2H), 7.7 (m, 1H), 7.8 (d, 1H), 8.1 (m, 2H), 8.4 (d, 1H), 9.0 (m, 1H), 11.01 (brs, 1H).

EXAMPLE 4

2-[(Aminocarbonyl)amino]-5-(2-benzothiophenyl)-3-thiophenecarboxamide

Prepared by the method of Example 1 (d) but using benzothiophene-2-boronic acid.

MS (ES) 316 (M–H)$^-$.

$^1$H NMR (DMSO-D6) 7.0 (m, 2H), 7.35 (m, 3H), 7.4 (s, 1H), 7.6 (s, 1H), 7.8 (d, 1H), 7.85 (m, 1,1H), 7.9 (d, 1H), 11.09 (s, 1H).

EXAMPLE 5

2-[(Aminocarbonyl)amino]-5-(3-benzothiophenyl)-3-thiophenecarboxamide

Prepared by the method of Example 1 (d) but using benzothiophene-3-boronic acid.

MS (ES) 316 (M–H)$^-$.

$^1$H NMR (DMSO-D6) 6.95 (m, 2H), 7.25 (m, 1H), 7.4 (m, 2H), 7.65 (s, 1H), 7.7 (s, 1H), 7.8 (m, 1H), 8.0 (d, 1H), 8.2 (d, 1H), 11.08 (brs, 1H).

EXAMPLE 6

2-[(Aminocarbonyl)amino]-5-(5-indolyl)-3-thiophenecarboxamide

Prepared by the method of Example 1 (d) but using indole-5-boronic acid.

MS (ES) 299 (M–H)$^-$.

$^1$H NMR (DMSO-D6) 6.4 (s, 1H), 6.8 (m, 2H), 7.2 (m, 1H), 7.3 (m, 3H), 7.6 (s, 1H), 7.65 (m, 1H), 7.7 (s, 1H), 10.91 (s, 1H), 11.0 (brs, 1H).

EXAMPLE 7

2-[(Aminocarbonyl)amino]-4-methyl-5-(1-benzodioxan-6-yl)-3-thiophenecarboxamide a) 2-Amino4-methyl-5-(1,4-benzodioxan-6-yl)-3-thiophencarboxamide 1,4-Benzodioxan-6-yl acetone (1.7 g), cyanoacetamide (0.84 g), sulphur (0.36 g) and morpholine (1 ml) in ethanol (5 ml) were stirred and heated at 55° C. for 6 h. The reaction mixture was cooled and screened from a little insoluble before adding to water (150 ml). The precipitated solid was filtered off, washed with water and then dried. The product was then triturated with ether and collected (1.0 g).

MS (EI) 266 (M)$^+$.

$^1$H NMR (DMSO-D6) 7.4 (2H, d), 7.3 (2H, d), 6.9 (2H, s), 6.8 (2H, s), 2.2 (3H, s).

b) 2-[(Aminocarbonyl)amino]-4-methyl-5-(1,4-benzodioxan-6-yl)-3-thiophenecarboxamide 2-Amino-4-methyl-5-(1,4-benzodioxan-6-yl)-3-thiophencarboxamide (0.44 g) was dissolved in tetrahydrofuran (10 ml), cooled to 0° C. and trichloroacetylisocyanate (0.11 ml) added dropwise with stirring. Stirring was continued for a further 30 minutes at room temperature and then a solution of ammonia in methanol (8 ml of a 10% solution) was added and stirring was continued for a further 3 h. The solvent was evaporated and the residue treated with ethyl acetate and the product filtered off.

MS (ES) 332 (M–H)$^-$.

$^1$H NMR (DMSO-D6) 2.2 (s, 3H), 4.25 (s, 4H), 6.7 (m, 2H), 6.8 (m, 2H), 6.9 (m, 1H), 7.2 (br, 1H), 10.01 (brs, 1H).

EXAMPLE 8

2-[(Aminocarbonyl)amino]-4-methyl-5-(3-indolyl)-3-thiophenecarboxamide

Prepared by the method of Example 7 but using indol-3-acetone.

MS (ES) 313 (M–H)$^-$.

$^1$HNMR (DMSO-D6) 2.2 (s, 3H), 6.65 (brs, 2H), 7.05 (m, 1H), 7.1 (m, 1H), 7.2 (m, 2H), 7.4 (m, 1H), 7.45 (d, 1H), 7.55 (d, 1H), 10.14 (brs, 1H), 11.3 (m, 1H).

EXAMPLE 9

2-[(Aminocarbonyl)amino]-4-methyl-5-(1,3-benzodioxolan-5-yl)-3-thiophenecarboxamide Prepared by the method of Example 7 but using 1,3-benzodioxolan-5-acetone.

MS (ES) 318 (M–H)$^-$.

$^1$H NMR (DMSO-D6) 2.2 (s, 3H), 6.05 (s, 2H), 6.8 (m, 1H), 6.9 (m, 1H), 6.95 (m, 1H), 7.1 (m, 2H), 7.2 (m, 2H).

EXAMPLE 10

2-[(Aminocarbonyl)amino]-5-(1H-indol-2-yl)thiophene-3-carboxamide a) The title compound was prepared by treating 2-[(aminocarbonyl)amino]-5-(1H-1-tert-butyloxycarbonylindol-2-yl)thiophene-3-carboxamide with a mixture of 90% trifluoroacetic acid/10% water at ambient temperature for 4 h. Evaporation gave a solid (250 mg) which was washed with water.

MS (ES) 301 (M+H)$^+$.

$^1$H NMR (DMSO-D6) 6.5 (s, 1H), 6.95 (m, 4H), 7.35 (m, 2H), 7.45 (d, 1H), 7.6 (s, 1H), 7.62 (brs, 1H), 10.9 (s, 1H), 11.32 (brs, 1H).

b) 2-[(Aminocarbonyl)amino]-5-(1H-1-tert-butyloxycarbonylindol-2-yl)thiophene-3-carboxamide The title compound (500 mg) was prepared from 1H-1-(tert-butoxycarbonyl)indol-2-yl boronic acid in a similar manner to Example 1 (d) except that the product was obtained as a solid by filtration of the reaction mixture and was washed sequentially with 2N sodium hydroxide solution, water and methanol.

MS (ES) 401 (M+H)$^+$.

$^1$H NMR (DMSO-D6) 1.4 (s, 9H), 6.7 (m, 1H), 6.95 (brs, 2H), 7.2 (m, 3H), 7.4 (m, 1H), 7.6 (s, 1H), 7.65 (brs, 1H), 8.0 (m, 1H), 11.04 (brs, 1H).

EXAMPLE 11

3[-(Aminocarbonyl)amino]-5-(1-benzothien-3-yl)thiophene-2-carboxamide a) 2-Bromothiophene-4-carboxylic acid Prepared according to the method as described in *J. Am. Chem. Soc.*, 1954, 76, 2445.

MS (ES) 205 (M–H)$^-$.

$^1$H NMR (DMSO-D6) 7.45 (s, 1H), 8.22 (s, 1H), 12.94 (brs, 1H).

b) 2-Bromo-4-(N-t-butyloxycarbonyl)aminothiophene

2-Bromothiophene4-carboxylic acid (3 g) was dissolved in dry warm t-butanol (24 ml). Triethylamine (2.02 ml) was added followed by diphenylphosphoryl azide (3.12 ml). The solution was heated slowly to reflux and heating continued at reflux overnight. The reaction mixture was then allowed to cool, poured into water (150 ml) and extracted with ethyl acetate (3×100 ml). The combined extracts were dried (MgSO$_4$), filtered and evaporated. The crude product was purified by column chromatography, eluting with 5% ethyl acetate in hexane, to give a white solid (1.69 g).

MS (ES) 276 (M–H)$^-$.

$^1$H NMR (DMSO-D6) 1.44 (s, 9H), 7.03 (s, 1H), 7.51 (s, 1H), 9.65 (s, 1H).

c) 5-Bromo-3-[(t-butyloxycarbonyl)amino]thiophene-2-carboxylic acid

2-Bromo-4-(N-t-butyloxycarbonyl)aminothiophene (1.68 g) was stirred in dry THF (45 ml) under argon and the solution was cooled to –78° C. Lithium diisopropylamide (7.55 ml, 2M solution) was added dropwise and stirring continued for 3.5 h. Powdered CO$_2$ (excess) was added and the mixture stirred for a further 10 minutes before allowing to warm to room temperature. Water (50 ml) was added, the THF was removed in vacuo and the aqueous phase was extracted with ethyl acetate (3×40 ml). The combined extracts were washed with 1M HCl solution (50 ml), water (50 ml) and brine (50 ml), dried (MgSO$_4$), filtered and the solvent evaporated. The residue was triturated with dichloromethane and the product collected by filtration as a pale yellow solid (1.57 g).

MS (ES) 320 (M–H)$^-$.

$^1$H NMR (DMSO-D6) 9.38 (s, 1H), 7.79 (s, 1H), 1.42, (s, 9H).

d) 5-Bromo-3-(t-butyloxycarbonyl)aminothiophene-2-carboxamide

5-Bromo-3-[(t-butyloxycarbonyl)amino]thiophene-2-carboxylic acid (0.80 g) was stirred in acetonitrile (80 ml). Hydroxybenztriazole (1.41 g) and 1-(3-dimethylaminopropyl)-3-ethylcarbodiimide hydrochloride (2.62 g) were added and stirring continued at room temperature for 10 minutes. Concentrated aqueous ammonia solution (8 ml) was added and the reaction mixture was heated to reflux for 1 h. The acetonitrile was removed by evaporation. Water (100 ml) was added and the mixture was sonicated and triturated. The resultant off-white solid was then collected by filtration, washed with water and dried under vacuum (0.763 g).

MS (ES) 319 (M–H)$^-$.

$^1$H NMR (DMSO-D6) 1.45 (s, 9H), 7.63 (brs, 2H), 7.78 (s, 1H), 10.40 (s, 1H).

e) 3-Amino-5-bromothiophene-2-carboxamide

5-Bromo-3-(t-butyloxycarbonyl)aminothiophene-2-carboxamide (0.76 g) was stirred in dichloromethane (30 ml). Trifluoroacetic acid (51 ml) was added, the solution was stirred at room temperature for 1 h, poured into saturated aqueous sodium hydrogen carbonate solution (200 ml) and extracted with dichloromethane (3×100 ml). The combined extracts were washed with brine (150 ml), dried (magnesium sulphate), filtered and evaporated to give a yellow solid (0.511 g).

MS (ES) 221 (M+H)$^+$.

$^1$H NMR (DMSO-D6) 6.50 (brs, 2H), 6.69 (s, 1H), 6.87 (brs, 2H).

f) 3-[(Aminocarbonyl)amino-5-bromothiophene-2-carboxamide

The title compound was prepared from 3-amino-5-bromothiophene-2-carboxamide in a similar manner to Example 1(b).

MS (ES) 264 (M+H)$^+$.

$^1$H NMR (DMSO-D6) 6.63 (brs, 2H), 7.41 (brs, 2H), 7.97 (s, 1H), 10.02 (s, 1H).

g) 3-[(Aminocarbonyl)amino-5-(1-benzothien-3-yl)thiophene-2-carboxamide

3-[(Aminocarbonyl)amino-5-bromothiophene-2-carboxamide (0.222 g) and 1-benzothien-3-ylboronic acid (0.449 g) were sonicated in 1,2-dimethoxyethane (15 ml) and saturated aqueous sodium hydrogen carbonate solution (3.5 ml) and purged with argon. Tetrakis(triphenylphosphine)-palladium (95 mg) was added and the mixture was heated at reflux with stirring for 4.5 h, then allowed to cool and stirred at room temperature overnight. The solution was filtered and washed through with 1,2-dimethoxyethane and water. The filtrate was concentrated in vacuo and taken up in dichloromethane (20 ml) and saturated aqueous sodium hydrogen carbonate solution (20 ml). The solid product was collected by filtration, washed with dichloromethane, water, diethyl ether and dried (226 mg).

MS (ES) 318 (M+H)$^+$.

$^1$H NMR (DMSO-D6) 6.60 (brs, 2H), 7.35–7.56 (m, 4H), 8.04 (s, 1H), 8.10 (t, 2H), 8.25 (s, 1H), 10.08 (s, 1H).

EXAMPLE 12

2-[(Aminocarbonyl)amino]-5-(2-morpholin-4-ylmethylbenzo[b]thiophen-5-yl)thiophene-3-carboxamide 4-(5-Bromobenzo[b]thiophen-2-ylmethyl)morpholine (Beilstein Reg. No. 1115497) (230 mg) in dry THF was treated with triisopropyl borate (291 mg) and was cooled under argon to <–70° C. with stirring. After dropwise addition of n-butyl lithium (0.921 ml, 1.6M in hexanes) the reaction was allowed to warm to room temperature. The solvent was evaporated and replaced with a mixture of dimethoxyethane (20 ml) and saturated aqueous sodium hydrogen carbonate (9 ml). To this mixture was added under argon 2-[(aminocarbonyl)amino]-5-bromothiophen-3-carboxamide (98 mg) and tetrakis-triphenyl phosphine palladium (0) (25 mg) and the reaction heated to 90° C. for 1.5 h. The reaction mixture was evaporated to remove the bulk of the organics and the residue distributed between 2M aqueous sodium hydroxide (30 ml) and dichloromethane. After filtering, the organic phase was separated and extracted with a fuither volume of sodium hydroxide solution (10 ml). The combined aqueous extracts were acidified to pH 8 and filtered. After drying the solid was triturated with diethyl ether and dried to give a powder (27 mg).

LCMS 417 (M+H)$^+$.

$^1$H NMR (DMSO-D6) 2.47 (m, 4H), 3.65 (m, 4H), 3.80 (s, 2H), 6.95 (brs, 2H), 7.3 (brs, 1H), 7.33 (s, 1H), 7.5 (m, 1H), 7.69 (brs, 1H), 7.75 (s, 1H), 7.91 (m, 2H), 11.0 (s, 1H).

EXAMPLE 13

2-[(Aminocarbonyl)amino]-5-[4-(2-morpholin-4-ylethoxy)-1-benzothien-2-yl]-3-thiophenecarboxamide a) The title compound was prepared from 4-[2-(1-benzothien-4-yloxy)ethyl]morpholine in a similar manner to Example 12, except that the reaction mixture was heated at 90° C. for 4 h. After removing the solvent in vacuo, the residue was treated with 3M sodium carbonate/dichloromethane and the solid filtered from the interface. Purification by preparative hplc gave the product.

MS (ES) 447 (M+H)$^+$.

¹HNMR (DMSO-D6) 2.5 (m, 4H), 2.8 (t, 2H), 3.55 (m, 4H), 4.25 (t, 2H), 7.0 (m, 3H), 7.15 (m, 2H), 7.35 (m, 3H), 7.8 (m, 1H), 11.05 (brs, 1H).

b) 4-[2-[(1-Benzothien-4-yloxy)ethyl]morpholine 4-(2-Chloroethyl)morpholine hydrochloride (0.74 g), 1-benzothiophene-4-ol (0.5 g) and potassium carbonate (1.1 g) in dimethylformamide (15 ml) were heated and stirred at 80° C. for 6 h. After cooling, the mixture was poured into water and extracted twice with ethyl acetate. The combined solvent phase was washed twice with brine, dried (magnesium sulphate) and evaporated to give the product (0.7 g).

MS (ES) 264 (M+H)$^+$.

$^1$H NMR (DMSO-D6) 2.5 (m, 4H), 2.8 (t, 2H), 3.55 (m, 4H), 4.25 (t, 2H), 6.9 (d, 1H), 7.25 (t, 1H), 7.4 (d, 1H), 7.55 (d, 1H), 7.6 (d, 1H).

c) 1-Benzothiophene-4-ol

The compound was prepared as described in *J.Amer.Chem.Soc.*, 1955, 77, 5939.

EXAMPLE 14

2-[(Aminocarbonyl)amino]-5-{2-[4-methylphenyl-sulphonyl]-1.2,3,4-tetrahydro isoquinolin-6-yl}thiophene-3-carboxamide a) The title compound was prepared from 6-bromo-2-[4-methylphenylsulphonyl]-1,2,3,4-tetrahydroisoquinoline in a similar manner to Example 13, except that the reaction mixture was heated at 80° C. for 18 h. After removing the solvent in vacuo, the residue was treated with 2M sodium hydroxide and dichloromethane and the separated aqueous phase was adjusted to pH 8 using 36% hydrochloric acid. The crude product was purified by preparative hplc.

MS (ES) 471 (M+H)$^+$.

$^1$H NMR (DMSO-D6) 2.4 (s, 3H), 2.8 (m, 2H), 3.2 (m, 2H), 4.1 (s, 2H), 6.9 (br, 2H), 7.15 (m, 1H), 7.3 (m, 1H),7.4 (m, 2H),7.5 (m, 1H), 7.7–7.9 (m, 5H), 11.0 (s, 1H).

b) 6-Bromo-2-[4-methylphenylsulphonyl]-1,2,3,4-tetrahydroisoquinoline

2-[3-Bromophenyl]-N-(4-methylphenylsulphonyl)ethylamine (7.44 g) was stirred in chloroform (100 ml) under argon at 5° C. during the sequential addition of 37–40% formaldehyde (3.5 ml) and phosphorus oxychloride (30 ml). The mixture was then refluxed for 3 h, cooled, poured into dichloromethane (250 ml)/saturated sodium bicarbonate (300 ml) and solid sodium bicarbonate (160 g) cautiously added in portions at 5° C. The aqueous phase was further extracted with dichloromethane and the combined organic phases washed with saturated sodium bicarbonate and water, dried (MgSO$_4$) and evaporated to give an oil, which crystallised from isohexane/toluene to give the product (3.48 g).

MS (ES) 365 (M)$^+$.

$^1$H NMR (CDCl$_3$) 2.43 (s, 3H), 2.89 (t, 2H), 3.34 (t, 2H), 4.18 (s, 2H), 6.89 (d, 1H), 7.23–7.30 (m, 2H obscured), 7.33 (d, 2H), 7.72 (d, 2H).

c) 2-[3-Bromophenyl]-N-(4-methylphenylsulphonyl)ethylamine

3-Bromophenylethylamine hydrochloride (9.44 g) was added to THF (60 ml) containing triethylamine (12.24 ml) and stirred-under argon at 5° C. during the portionwise addition over 15 minutes of 4-methylphenylsulphonyl chloride (11.44 g). The slurry was diluted with THF (50 ml) and stirred for 16 h. The solid was filtered off, washed with THF and the filtrate evaporated. The residue was dissolved in ethyl acetate, washed with 1N hydrochloric acid, water, brine and dried (MgSO$_4$). Chromatography on flash silica, eluting with 0 to 25% ethyl acetate in isohexane gave the product (9.67 g).

MS (ES) 352 (M–H)$^-$.

$^1$H NMR (CDCl$_3$) 2.44 (s, 3H), 2.74 (t, 2H), 3.23 (q, 2H), 4.36 (t, 1H), 7.03 (d, 1H), 7.14 (t, 1H), 7.17 (m, 1H), 7.30 (d, 2H), 7.35 (dd, 1H), 7.69 (dd, 2H).

d) 3-Bromophenylethylamine Hydrochloride

The free base of the title compound has CAS Registry Number 58971-11-2 and Beilstein Registry Number 2716071.

EXAMPLE 15

3-[(Aminocarbonyl)amino]-5-(1-benzothien-2-yl)thiophene-2-carboxamide

The title compound was prepared from 3-[(aminocarbonyl)amino-5-bromothiophene-2-carboxamide and 1-benzothien-2-ylboronic acid in a similar manner to Example 11 (g).

MS (ES) 318 (M+H)$^+$.

$^1$H NMR (DMSO-D6) 6.64 (brs, 2H), 7.33–7.47(m, 2H), 7.49 (brs, 2H), 7.71 (s, 1H), 7.80–7.90 (m, 1H), 7.90–8.02 (m, 1H), 8.23 (s, 1H), 10.05 (s, 1H).

Pharmacological Evaluation of Compounds

IKK2 Filter Kinase Assay

Compounds were tested for inhibition of IKK2 using a filter kinase assay. The test compounds were dissolved to 10 mM in dimethylsulphoxide (DMSO). The compounds were then diluted 1 in 40 in kinase buffer (50 mM Tris, pH 7.4 containing 0.1 mM EGTA, 0.1 mM sodium orthovanadate and 0.1% β-mercaptoethanol). 1 in 3 serial dilutions were made from this solution with 2.5% DMSO in kinase buffer. 20 μl of compound dilution was added to wells of a 96 well plate in duplicate. 20 μl 2.5% DMSO in kinase buffer instead of compound was added to control wells (0% inhibition). 20 μl 0.5 M EDTA was added instead of compound to background wells (100% inhibition).

10 μl of a mixture of magnesium acetate, unlabelled ATP, and $^{33}$P-labelled ATP was added to each well made such that the final concentration was 10 mM magnesium acetate, 1 μM ATP and 0.1 μCi $^{33}$P ATP. 20 μl of a mixture of IKK2 (0.15 μg/well), 1-53 GST-IκB (0.5 μg/well) and bovine serum albumin (BSA) (8.5 μg/well) was added to each well to start the reaction. The final reaction volume was 50 μl.

The kinase reactions were incubated at 21° C. for 80 minutes and the reaction stopped by precipitating the protein by the addition of an equal volume (50 μl) of 20% trichloroacetic acid (TCA). The precipitate was allowed to form for 10 minutes and then filtered onto a GF/C unifilter 96 well plate. Each filter was washed twice with approximately 1 ml 2% TCA. The filter plate was dried at 30–40° C. for 60 minutes, 20 μl scintillant was added to each well and the plate sealed and radioactivity counted on a Packard Top-count microplate scintillation counter.

When tested in the above assay, the compounds of Examples 1 to 15 gave IC$_{50}$ values of less than 10 μM indicating that they are expected to show useful therapeutic activity.

IKK1 Filter Kinase Assay

The selectivity of compounds was assessed by testing them for inhibition of IKK1 using a filter kinase assay. The assay conditions were identical to the IKK2 filter kinase assay except that a mixture of IKK1 (0.25 µg/well) and 1-53 GST IκB (9 µg/well) was added to each well to start the reaction.

Inhibition of LPS-Induced TNFα Production by PBMCs

The effect of test compounds on nuclear factor kappa B (NFκB) activation in cells was assessed by measuring inhibition of tumour necrosis factor alpha (TNFα) production by human peripheral blood mononuclear cells (PBMCs) stimulated by bacterial lipopolysaccharide (LPS).

Human blood (250 ml), anticoagulated with heparin, was collected from healthy volunteers. Aliquots of blood (25 ml) were layered on 20 ml Lymphoprep (Nycomed) in 50 ml polypropylene centrifuge tubes. The tubes were centrifuged (Sorval RT600B) at 2,500 rpm for 30 minutes. The cloudy layer containing PBMCs was collected with a fine tipped Pasteur pipette, transferred into 8 clean polypropylene centrifuge tubes (approximately 10 ml per tube) and diluted to 50 ml with phosphate-buffered saline (PBS). These tubes were centrifuged at 2,000 rpm for 8 minutes. PBS (10 ml) was added to each cell pellet and the cells were gently re-suspended. The cells were pooled in 4 centrifuge tubes, PBS was added to each tube to make the volume up to 50 ml and the tubes were centrifuged at 1,400 rpm for 8 minutes. The cell pellets were again re-suspended in 10 ml PBS, pooled in 2 centrifuge tubes, the volume made up to 50 ml with PBS and the tubes centrifuged at 900 rpm for 10 minutes.

The final cell pellets were gently re-suspended in 10 ml tissue culture medium (RPMI containing 1% heat-inactivated human serum, L-glutamine and penicillin and streptomycin), combined into 1 tube and the volume made up to 30 ml with RPMI medium. The cells were counted and the cell suspension was diluted to $2.6 \times 10^6$ cells/ml.

Test compounds were dissolved in DMSO to 10 mM and diluted 1 in 250 (40 µM) with RPMI medium. The compounds were then serially diluted 1 in 3 with 0.4% DMSO in RPMI medium. Aliquots of test compound dilutions (50 µl) were transferred to the wells of a 96-well plate. Control wells contained 0.4% DMSO in RPMI instead of compound.

Aliquots of the cell suspension (100 µl) were added to each well and the plates incubated at 37° C. for 30 minutes. 50 µl of 40 µg/ml LPS (Sigma, L-4130) was added to wells to stimulate TNFα production by the cells and the plates were incubated overnight at 37° C. RPMI medium (50 µl) was added to negative control wells instead of LPS. The final incubation volume was 200 µl.

Plates were centrifuged for 4 minutes at 1,200 rpm and supernatants were removed for measurement of TNFα concentration. Viability of the remaining cell pellet was measured using WST-1 reagent (Boehringer Mannheim, 1044807). 100 µl RPMI medium containing 10 µl WST-1 reagent was added to each well and the plates were incubated for 0.5 to 3 h. The absorbance at 450 nm was then measured using a 96-well plate spectrophotometer.

TNFα in the supernatants (freshly harvested or stored frozen at −20° C.) were measured using an enzyme-linked immmunosorbant assay (ELISA). The ELISA plate was prepared by coating the wells of a 96 well plate with a sheep anti-human TNFα monoclonal antibody (100 µl of 1 µg/ml antibody diluted in coating buffer; 0.5 M carbonate/bicarbonate buffer, pH 9.6 containing 0.2 g/l sodium azide) and incubating overnight at 4° C. Blank wells were not coated.

The wells were washed once with 0.1% BSA in PBS containing 0.05% Tween (PBS/Tween) then incubated for 1 h at room temperature with 1% BSA in coating buffer (200 µl). The wells were then washed 3 times with 0.1% BSA in PBS/Tween.

The samples of supernatant from the PBMC incubation were diluted 1 in 3 with 1% BSA in PBS/Tween. 100 µl aliquots of these dilutions were added to the ELISA plate. Other wells contained 100 µl TNFα standard (10, 3.3, 1.1, 0.37, 0.12, 0.04, 0.014 and 0 ng/ml). The ELISA plate was incubated at room temperature for 2 h before the wells were washed 3 times with 0% BSA in PBS/Tween. A rabbit anti-human TNFα antibody (100 µl of a 2.5 µg/ml solution) was added to each well and the plate incubated at room temperature for 1.5 h. The wells were then washed 3 times with 0.1% BSA in PBS/Tween. Goat anti-rabbit IgG-horse radish peroxidase conjugate (ICN, 674371; 100 µl of a 1 in 10,000 dilution) was added to each well and the plate incubated at room temperature for 1.5 h. The wells were washed 3 times with 0.1% BSA in PBS/Tween.

Peroxidase substrate was prepared by dissolving a 1 mg TMB tablet (Sigma, T-5525) in 100 µl DMSO (100 µl) and adding this and 36 µl UHPO (BDH, 30559; 1 g tablet dissolved in 25 ml distilled water) to 10 ml 0.1M citrate/acetate buffer, pH6. 100 µl substrate was added to each well and the plate incubated in the dark at room temperature for approximately 30 minutes. The reaction was stopped by adding 25 µl 2 M sulphuric acid to each well. The absorbance at 450 nm was measured in a 96 well plate spectrophotometer.

The invention claimed is:

1. A compound of formula (I)

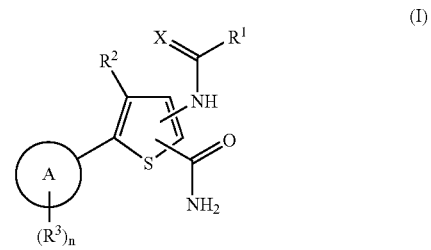

in which:

R¹ represents $NH_2$ or R¹ represents a methyl group optionally substituted by one or more groups selected independently from $C_1$–$C_4$ alkyl, $C_3$–$C_6$ cycloalkyl, halogen, hydroxyl, $C_1$–$C_4$ alkoxy, $S(O)_v CH_3$ and $NR^4 R^5$;

X represents O or S;

R² represents hydrogen, halogen, cyano, nitro, —$NR^6 R^7$, —$CONR^6 R^7$, —$COOR^6$—$NR^6$ $COR^7$, —$S(O)_m R^6$, —$SO_2 NR^6 R^7$, —$NR^6$ $SO_2$ $R^7$, $C_1$–$C_2$ alkyl, trifluoromethyl, $C_2$–$C_3$ alkenyl, $C_2$–$C_3$ alkynyl, trifluoromethoxy, $C_1$–$C_2$ alkoxy or $C_1$–$C_2$ alkanoyl;

A represents a fused bicyclic ring system wherein one ring is a phenyl ring or a 5- to 7-membered heteroaromatic ring containing one to three heteroatoms selected independently from O, N and S; and the other ring is either a fused phenyl ring or a fused 5- to 7-membered heteroaromatic ring containing one to three heteroatoms selected independently from O, N and S; or a fused 5- to 7-membered saturated ring optionally incorporating one to three heteroatoms selected independently from oxygen, nitrogen and sulphur; said fused bicyclic ring system being optionally substituted by one or more substituents selected independently from halogen, cyano, nitro, —NR$^8$COR$^9$, —S(O)$_s$R$^8$, —SO$_2$NR$^8$R$^9$, —NR$^8$SO$_2$R$^9$ and C$_1$–C$_6$ alkyl;

n represents an integer 0, 1 or 2; and when n represents 2, each R$^3$ group may be selected independently;

R$^3$ represents a group —W—Y—Z wherein:

W represents O, S(O)$_r$, NR$^{13}$, CH$_2$, —CH$_2$—O— or a bond;

Y represents a bond or Y represents a group —(CH$_2$)$_p$—X—(CH$_2$)$_q$— wherein p and q independently represent an integer 0, 1 or 2; and X represents O, —CO— or CR$^{14}$R$^{15}$ R$^{14}$ and R$^{15}$ independently represent H, CH$_3$ or F;

or R$^{14}$ represents H or CH$_3$ and R$^{15}$ represents hydroxyl or OCH$_3$;

or the group CR$^{14}$R$^{15}$ together represents a C$_3$–C$_6$ cycloalkyl ring;

Z represents:

(a) a phenyl ring or a 5- or 6-membered heteroaromatic ring containing one to three heteroatoms selected independently from O, N and S; said phenyl or heteroaromatic ring being optionally substituted by one or more substituents selected independently from halogen, cyano, —NR$^{16}$R$^{17}$, —CONR$^{16}$R$^{17}$, —COOR$^{16}$, —COR$^{16}$—NR$^{16}$COR$^{17}$, —S(O)$_u$R$^{16}$, —SO$_2$NR$^{16}$R$^{16}$—NR$^{16}$SO$_2$R$^{17}$, hydroxyl, C$_2$–C$_6$ alkenyl, C$_2$–C$_6$ alkynyl, C$_1$–C$_6$ alkyl and C$_1$–C$_6$ alkoxy; said alkyl or alkoxy group being optionally further substituted by one or more groups selected from halogen, cyano, hydroxyl, C$_1$–C$_4$ alkoxy and NR$^{18}$R$^{19}$; or (b) a saturated 3- to 7-membered ring optionally incorporating one or two heteroatoms selected independently from O, N and S, and optionally incorporating a carbonyl group; said saturated ring being optionally substituted by one or more substituents selected independently from halogen, cyano, —NR$^{16}$R$^{17}$, —CONR$^{16}$R$^{17}$, —COOR$^{16}$, —COR$^{16}$, —NR$^{16}$COR$^{17}$, —S(O)$_u$R$^{16}$—SO$_2$NR$^{16}$R$^{17}$, —NR$^{16}$SO$_2$R$^{17}$, hydroxyl, C$_2$–C$_6$ alkenyl, C$_2$–C$_6$ alkynyl, C$_1$–C$_6$ alkyl and C$_1$–C$_6$ alkoxy; said alkyl or alkoxy group being optionally further substituted by one or more groups selected from halogen, cyano, hydroxyl, C$_1$–C$_4$ alkoxy and NR$^{18}$R$^{19}$; or (c) Z represents hydroxyl, C$_1$–C$_6$ alkoxy, CF$_3$, CHF$_2$, CH$_2$F or NR$^{20}$R$^{21}$ where R$^{20}$ and R are independently hydrogen or C$_1$–C$_6$ alkyl optionally substituted by C$_1$–C$_4$ alkoxy;

R$^4$ and R$^5$ independently represent H or C$_1$–C$_4$ alkyl; or the group NR$^4$R$^5$ represents a 5- or 6-membered saturated azacyclic ring optionally containing a further O, S or NR$^{23}$ group; where R$^{23}$ is hydrogen or C$_1$–C$_4$ alkyl;

R$^6$ and R$^7$ independently represent H or C$_1$–C$_2$ alkyl;

R$^8$ and R$^9$ independently represent H or C$_1$–C$_6$ alkyl;

R$^{13}$ represents H or C$_1$–C$_4$ alkyl;

R$^{16}$ and R$^{17}$ independently represent H or C$_1$–C$_6$ alkyl; or the group NR$^{16}$R$^{17}$ represents a 5-6-membered saturated azacyclic ring optionally containing a further O, S or NR$^{24}$ group; where R$^{24}$ is hydrogen or C$_1$–C$_6$ alkyl;

R$^{18}$ and R$^{19}$ independently represent H or C$_1$–C$_4$ alkyl; or the group NR$^{18}$R$^{19}$ represents a 5-6-membered saturated azacyclic ring optionally containing a further O, S or NR$^{25}$ group; where R$^{25}$ is hydrogen or C$_1$–C$_4$ alkyl;

m, r, s, u and v independently represent an integer 0, 1 or 2;

and pharmaceutically acceptable salts thereof.

2. A compound of formula (I), according to claim 1, wherein X represents oxygen.

3. A compound of formula (I), according to claim 1, wherein R$^1$ represents NH$_2$.

4. A compound of formula (I), according to claim 1, in which R$^2$ represents H or methyl.

5. A compound of formula (I), according to claim 1, selected from:

2-[(aminocarbonyl)amino]-5-(2-benzofuranyl)-3-thiophenecarboxamide;

2-[(aminocarbonyl)amino]-5-(3-quinolinyl)-3-thiophenecarboxamide;

2-[(aminocarbonyl)amino]-5-(8-quinolinyl)-3-thiophenecarboxamide;

2-[(aminocarbonyl)amino]-5-(2-benzothiophenyl)-3-thiophenecarboxamide;

2-[(aminocarbonyl)amino]-5-(3-benzothiophenyl)-3-thiophenecarboxamide;

2-[(aminocarbonyl)amino]-5-(5-indolyl)-3-thiophenecarboxamide;

2-[(aminocarbonyl)amino]-4-methyl-5-(1,4-benzodioxan-6-yl)-3-thiophenecarboxamide;

2-[(aminocarbonyl)amino]-4-methyl-5-(3-indolyl)-3-thiophenecarboxamide;

2-[(aminocarbonyl)amino]-4-methyl-5-(1,3-benzodioxo-5-yl)-3-thiophenecarboxamide;

2-[(aminocarbonyl)amino]-5-(1H-indol-2-yl)thiophene-3-carboxamide;

3-[(aminocarbonyl)amino]-5-(1-benzothien-3-yl)thiophene-2-carboxamide;

2-[(aminocarbonyl)amino]-5-(2-morpholin-4-ylmethyl-benzo[b]thiophen-5-yl)thiophene-3-carboxamide;

2-[(aminocarbonyl)amino]-5-[4-(2-morpholin-4-ylethoxy)-1-benzothien-2-yl]-3-thiophenecarboxamide;

2-[(aminocarbonyl)amino]-5-{2-[4-methylphenylsulphonyl]-1,2,3,4-tetrahydro isoquinolin-6-yl} thiophene-3-carboxamide;

3-[(aminocarbonyl)amino]-5-(1-benzothien-2-yl)thiophene-2-carboxamide;

and pharmaceutically acceptable salts thereof.

6. A process for the preparation of a compound of formula (I), according to claim 1, which comprises:

(a) reaction of a compound of formula (II):

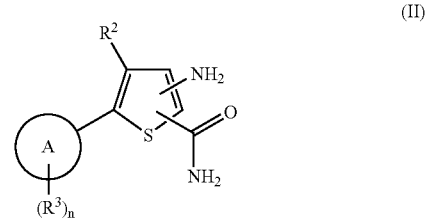

wherein A, R$^2$, R$^3$ and n are as defined in claim 1 with an isocyanate or an isothiocyanate or an acyl derivative, R$^1$—CO—L, where L is a leaving group; or (b) reaction of compound of formula (III)

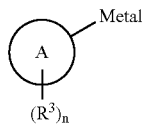

wherein R³, n and A are as defined in claim 1 with a compound of formula (IV)

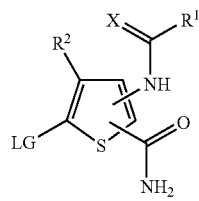

wherein X, R¹ and R² are as defined in claim 1 and LG represents a leaving group; or (c) reaction of compound of formula (V)

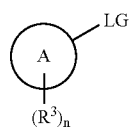

wherein R³, n and A are as defined in claim 1 and LG represents a leaving group, with a compound of formula (VI)

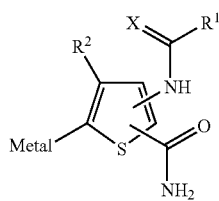

wherein X, R¹ and R² are as defined in claim 1;

and where necessary converting the resultant compound of formula (I), or another salt thereof, into a pharmaceutically acceptable salt thereof; or converting the resultant compound of formula (I) into a further compound of formula (I); and where desired converting the resultant compound of formula (I) into an optical isomer thereof.

7. A pharmaceutical composition comprising a compound of formula (I), or a pharmaceutically acceptable salt thereof, as claimed in claim 1 in association with a pharmaceutically acceptable adjuvant, diluent or carrier.

8. A process for the preparation of a pharmaceutical composition as claimed in claim 7 which comprises mixing a compound of formula (I), or a pharmaceutically acceptable salt thereof, as claimed claim 1 with a pharmaceutically acceptable adjuvant, diluent or carrier.

9. A method of treatment or prophylaxis of a patient having an inflammatory disease, the method comprising:
    using a compound of formula (I), or a pharmaceutically acceptable salt thereof, as claimed in claim 1 in the treatment or prophylaxis of the inflammatory disease.

10. The method as claimed in claim 9 wherein the inflammatory disease is asthma.

11. The method as claimed in claim 9 wherein the inflammatory disease is rheumatoid arthritis.

12. The method as claimed in claim 9 wherein the inflammatory disease is multiple sclerosis.

13. The method as claimed in claim 9 wherein the disease is chronic obstructive pulmonary disease.

14. The method as claimed in claim 9 wherein the disease is cancer.

15. A method of treating, or reducing the risk of, diseases or conditions in which inhibition of IKK2 activity is beneficial which comprises administering to a person suffering from or at risk of said disease or condition a therapeutically effective amount of a compound of formula (I), or a pharmaceutically acceptable salt thereof, as claimed in claim 1.

* * * * *